(12) United States Patent
Konishi et al.

(10) Patent No.: US 9,857,304 B2
(45) Date of Patent: Jan. 2, 2018

(54) MEASURING METHOD AND MEASURING SYSTEM OF BROMATE ION CONCENTRATION

(71) Applicant: METAWATER CO., LTD., Tokyo (JP)

(72) Inventors: Natsumi Konishi, Tokyo (JP); Eri Hasegawa, Tokyo (JP)

(73) Assignee: Metawater Co., Ltd., Chiyoda-Ku (JP)

( * ) Notice: Subject to any disclaimer, the term of this patent is extended or adjusted under 35 U.S.C. 154(b) by 0 days.

(21) Appl. No.: 15/418,885

(22) Filed: Jan. 30, 2017

(65) Prior Publication Data

US 2017/0138853 A1 May 18, 2017

Related U.S. Application Data

(63) Continuation of application No. PCT/JP2015/002911, filed on Jun. 10, 2015.

(30) Foreign Application Priority Data

Sep. 9, 2014 (JP) .................. 2014-183520

(51) Int. Cl.
*G01N 21/64* (2006.01)
*G01N 33/18* (2006.01)

(52) U.S. Cl.
CPC ....... *G01N 21/643* (2013.01); *G01N 21/6428* (2013.01); *G01N 33/182* (2013.01); *G01N 2201/13* (2013.01); *Y10T 436/193333* (2015.01)

(58) Field of Classification Search
CPC .. G01N 21/64; G01N 21/6428; G01N 21/643; G01N 21/6432; G01N 21/6439; G01N 2201/13; G01N 30/02; G01N 30/48; G01N 33/18; G01N 33/182; Y10T 436/14; Y10T 436/141111; Y10T 436/145555; Y10T 436/147777; Y10T 436/15; Y10T 436/153333; Y10T 436/19; Y10T 436/193333
USPC ..... 436/92, 96, 98, 100, 101, 124, 125, 161, 436/164, 172; 422/69, 70, 82.05, 82.08
See application file for complete search history.

(56) References Cited

U.S. PATENT DOCUMENTS 8,778,691 B2 * 7/2014 Igarashi ............... G01N 21/643
436/101
2010/0330694 A1 12/2010 Igarashi et al.
2013/0337572 A1 12/2013 Kita et al.
2014/0113381 A1 4/2014 Konishi et al.

FOREIGN PATENT DOCUMENTS

JP 2013-024807 A1 2/2013
JP 2014-002007 A1 1/2014
WO 2009/116554 A1 9/2009

OTHER PUBLICATIONS

International Search Report and Written Opinion (Application No. PCT/JP2015/002911) dated Sep. 8, 2015.
English Translation of International Preliminary Report on Patentability, International Application No. PCT/JP2015/002911, dated Mar. 14, 2017 (10 pages).

* cited by examiner

Primary Examiner — Maureen Wallenhorst
(74) Attorney, Agent, or Firm — Burr & Brown, PLLC (57) ABSTRACT

A measuring method of bromate ion concentration includes a first fluorescence intensity measuring process including a process of passing hydrochloric acid through an anion exchanger to elute bromate ions adsorbed to the anion exchanger into the hydrochloric acid and a process of measuring the fluorescence intensity of the hydrochloric acid passed through the anion exchanger, a second fluorescence intensity measuring process including a process of passing a hydrochloric acid solution containing a fluorescent substance whose fluorescence intensity changes due to coexistence of bromate ions through an anion exchanger to elute bromate ions adsorbed to the anion exchanger into the hydrochloric acid solution and a process of measuring the fluorescence intensity of the hydrochloric acid solution passed through the anion exchanger, and a calculation process determining the bromate ion concentration in the water sample by using the difference between the fluorescence intensities of the hydrochloric acid solution and the hydrochloric acid.

8 Claims, 1 Drawing Sheet

MEASURING METHOD AND MEASURING SYSTEM OF BROMATE ION CONCENTRATION

TECHNICAL FIELD

This disclosure relates to a method and a system of measuring the bromate ion concentration in a water sample.

BACKGROUND

The potassium bromate, which is a bromate, has been known as a compound having carcinogenic potential for humans. On the other hand, in water purification plants and the like, advanced water treatment employing ozonation and the like has been performed. However, when the water containing bromide ion ($Br^-$) such as river water is treated with oxidation such as ozonation and the like, bromate ion ($BrO_3^-$) is produced as a reaction by-product. Thus, in recent years, with respect to the concentration of bromate ions contained in water such as tap water and the like, reference values have been defined in the water quality standard and the like, and the bromate ion concentration in the water has been measured.

Here, in Japan and the like, as a measuring method of bromate ion concentration in the water, the ion chromatograph-post column method (IC-PC method) has been used as an official method. However, in the IC-PC method, bromate ions separated from a water sample using an anion-exchange column react with bromide ions ($Br^-$) under acid condition to convert the bromate ions into tribromide ions ($Br_3^-$), and after that, the ultraviolet absorbance of the produced tribromide ions is measured, thereby the quantity of bromate ions is determined. Therefore, the IC-PC method had a problem of complicated operation and being unsuitable for a continuous measurement of bromate ion concentration.

Therefore, in recent years, as a method by which the bromate ion concentration in the water can be measured with a simple operation, a quantitative method has been proposed in which a fluorescent substance such as trifluoperazine (TFP) whose fluorescence intensity changes in response to the bromate ion concentration is used. More specifically, in Patent Literature 1, for example, a method has been proposed in which, first, bromate ions in a water sample is selectively adsorbed to an anion-exchange column, then a hydrochloric acid solution containing TFP as a fluorescent substance is passed through the anion-exchange column to elute bromate ions into the hydrochloric acid solution, after that, the fluorescence intensity of the hydrochloric acid solution containing the bromate ions eluted is measured, and finally, the measured value of the fluorescence intensity is compared with the previously prepared calibration curve, thereby the bromate ion concentration in the water sample is calculated. According to the measuring method described in this Patent Literature 1, a measurement is made after the bromate ions are selectively adsorbed to the anion-exchange column, and as a result of this, a measured value of the fluorescence intensity can be prevented from being influenced by interfering substances such as iodate ions and the like coexisting in the water sample. Therefore, according to the measuring method described in Patent Literature 1, the bromate ion concentration can be measured accurately. Furthermore, according to the measuring method described in Patent Literature 1, it is not necessary to convert the bromate ions desorbed from the anion-exchange column into tribromide ions ($Br_3^-$) as is in the case of the IC-PC method, thus the bromate ion concentration in the water can be measured with a simple operation.

CITATION LIST

Patent Literature

PTL 1: JP2014-002007 A

SUMMARY

Technical Problem

However, the measuring method of bromate ion concentration described in the above described Patent Literature 1 still has room to improve the measuring accuracy of bromate ion concentration. More specifically, the measuring method described in Patent Literature 1 still has room to improve the measuring accuracy to the same level as that the IC-PC method used as an official method in Japan and the like has achieved.

The inventors therefore provide a measuring method and a measuring system of bromate ion concentration capable of further improving the measuring accuracy of bromate ion concentration using a fluorescent substance.

Solution to Problem

The inventors of this disclosure have keenly examined the measuring performance for the purpose of solving the above described problem, and found out that, when using the method described in Patent Literature 1, even in the case where the anion-exchange column that selectively adsorbs bromate ions is used, the coexisting substances other than bromate ions are adsorbed to the anion-exchange column and the coexisting substances are eluted into the hydrochloric acid solution together with bromate ions, which eventually influences the measured value of the fluorescence intensity and the measuring accuracy of the bromate ion concentration. Then the inventors further examined the measuring performance and found out that the coexisting substances, unlike bromate ions, do not change the fluorescence intensity of the fluorescent substance, but when the excitation light is irradiated to them, the coexisting substances are excited and emit light, which may cause an error in measured values of the fluorescence intensity and the bromate ion concentration. Basing on these findings, the inventors completed this disclosure.

That is, to advantageously solve the above described problem, the present disclosure provides a measuring method of bromate ion concentration including the processes from (1) to (4) described below:

(1) A first fluorescence intensity measuring process including a process of passing a water sample through an anion exchanger that adsorbs bromate ions, a process of passing hydrochloric acid through the anion exchanger to elute bromate ions adsorbed to the anion exchanger into the hydrochloric acid, and a process of measuring the fluorescence intensity of the hydrochloric acid passed through the anion exchanger;

(2) A second fluorescence intensity measuring process including a process of passing a water sample through an anion exchanger that adsorbs bromate ions, a process of passing a hydrochloric acid solution containing a fluorescent substance whose fluorescence intensity changes due to the coexistence of bromate ions through the anion exchanger to elute bromate ions adsorbed to the anion exchanger into the hydrochloric acid solution, and a process of measuring the fluorescence intensity of the hydrochloric acid solution passed through the anion exchanger;

(3) A calculation process of calculating a difference between the fluorescence intensity of the hydrochloric acid solution measured in the second fluorescence intensity measuring process and the fluorescence intensity of the hydrochloric acid measured in the first fluorescence intensity measuring process; and (4) A bromate ion concentration determination process of determining the bromate ion concentration in the water sample by using the difference between the fluorescence intensities calculated in the calculation process and a calibration curve.

As described above, if the bromate ion concentration in the water sample is determined by using the difference between the fluorescence intensity of the hydrochloric acid solution containing the fluorescent substance and that of the hydrochloric acid containing no fluorescent substance, each passed through the anion exchanger, the influence of coexisting substances on the measuring accuracy of the bromate ion concentration is reduced, and as a result, the measuring accuracy of the bromate ion concentration can be further improved.

It is preferable that the disclosed measuring method of the bromate ion concentration further includes the following processes from (5) to (7):

(5) A third fluorescence intensity measuring process including a process of passing a standard water sample whose concentration is known through an anion exchanger that adsorbs bromate ions, a process of passing hydrochloric acid through the anion exchanger to elute bromate ions adsorbed to the anion exchanger into the hydrochloric acid, and a process of measuring the fluorescence intensity of the hydrochloric acid passed through the anion exchanger;

(6) A fourth fluorescence intensity measuring process including a process of passing a standard water sample whose concentration is known through an anion exchanger that adsorbs bromate ions, a process of passing a hydrochloric acid solution containing a fluorescent substance whose fluorescence intensity changes due to the coexistence of bromate ions through the anion exchanger to elute bromate ions adsorbed to the anion exchanger into the hydrochloric acid solution, and a process of measuring the fluorescence intensity of the hydrochloric acid solution passed through the anion exchanger; and (7) A calibration curve preparation process, in which the third fluorescence intensity measuring process and the fourth fluorescence intensity measuring process are performed with respect to a plurality of standard water samples whose bromate ion concentrations are different from each other and a calibration curve is prepared by using the differences between the fluorescence intensities of the hydrochloric acid solutions passed through the anion exchanger measured in the fourth fluorescence intensity measuring process and those of the hydrochloric acid passed through the anion exchanger measured in the third fluorescence intensity measuring process.

As described above, by using a calibration curve prepared by using the differences between the fluorescence intensity of the hydrochloric acid solution containing the fluorescent substance and that of the hydrochloric acid containing no fluorescent substance, each passed through the anion exchanger, the measuring accuracy of bromate ion concentration can be further improved.

Further, when the bromate ion concentration in a water sample is continuously measured using the disclosed measuring method of bromate ion concentration, it is preferable that the first fluorescence intensity measuring process, the second fluorescence intensity measuring process, the calculation process and the determination process of bromate ion concentration are repeatedly performed. When the bromate ion concentration in a water sample is continuously measured, it is not necessary to perform the first fluorescence intensity measuring process each time when the second fluorescence intensity measuring process is performed, and the previously measured fluorescence intensity of the hydrochloric acid containing no fluorescent substance passed through the anion exchanger can be used. However, when all of the processes are repeatedly performed as described above, a decrease in the measuring accuracy of bromate ion concentration due to the changes in water quality of the water samples over time can be prevented.

It should be noted that, in this disclosure, it does not matter which of the first fluorescence intensity measuring process and the second fluorescence intensity measuring process is performed first.

Further, to solve the above described problem advantageously, the present disclosure provides a measuring system of bromate ion concentration including an anion exchanger that adsorbs bromate ions, a water sample supply device that passes a water sample through the anion exchanger, a hydrochloric acid supply device that passes hydrochloric acid through the anion exchanger, a hydrochloric acid solution supply device that passes a hydrochloric acid solution containing a fluorescent substance whose fluorescence intensity changes due to the coexistence of bromate ions through the anion exchanger, a fluorescence intensity measuring device that measures the fluorescence intensity of the liquid passed through the anion exchanger, and a bromate ion concentration determination device that has a calculation unit that calculates the difference between the fluorescence intensity of the hydrochloric acid solution passed through the anion exchanger measured with the fluorescence intensity measuring device and that of the hydrochloric acid passed through the anion exchanger measured with the fluorescence intensity measuring device, a storage unit that stores a calibration curve, and determines the bromate ion concentration in the water sample by using the differences between the fluorescence intensities calculated by the calculation unit and a calibration curve stored in the storage unit. As described above, the hydrochloric acid supply device that passes hydrochloric acid containing no fluorescent substance through an anion exchanger is provided together with the bromate ion concentration determination device, and as a result, the bromate ion concentration in the water sample can be calculated by using the differences between the fluorescence intensity of the hydrochloric acid solution containing a fluorescent substance and that of the hydrochloric acid containing no fluorescent substance, each passed through the anion exchanger. As a result, the influence of the coexisting substances on the measuring accuracy of bromate ion concentration is decreased, and the measuring accuracy of bromate ion concentration can be further improved.

Here, in the disclosed measuring system of bromate ion concentration, it is preferable that the hydrochloric acid solution supply device includes a storage tank for storing a hydrochloric acid solution obtained by mixing a fluorescent substance and hydrochloric acid and a hydrochloric acid solution supply line that supplies a hydrochloric acid solution from the storage tank to the anion exchanger. As described above, if a storage tank that stores a hydrochloric acid solution prepared by mixing a fluorescent substance and hydrochloric acid beforehand is provided, when it is compared with the case where a hydrochloric acid solution is prepared by mixing a fluorescent substance and hydrochloric acid in the measuring system, a hydrochloric acid solution with a desired concentration of fluorescent substance can be supplied stably and at low cost.

Further, it is preferable that the disclosed measuring system of bromate ion concentration further includes a standard water sample supply device that passes a standard water sample whose bromate ion concentration is known through an anion exchanger, and the storage unit stores a calibration curve prepared by using the differences between the fluorescence intensity of the hydrochloric acid measured by the fluorescence intensity measuring device by passing the hydrochloric acid through the anion exchanger with the hydrochloric acid supply device after a standard water sample from the standard water sample supply device being passed through the anion exchanger, and that of the hydrochloric acid solution measured by the fluorescence intensity measuring device by passing the hydrochloric acid solution through the anion exchanger with the hydrochloric acid solution supply device after a standard water sample from the standard water sample supply device being passed through the anion exchanger. As described above, a standard water sample supply device is provided and a calibration curve prepared by using the differences between the fluorescence intensity of the hydrochloric acid solution containing a fluorescent substance and that of the hydrochloric acid containing no fluorescent substance, each passed through the anion exchanger, is stored in the storage unit for use, and as a result of this, the measuring accuracy of bromate ion concentration can be further improved.

Advantageous Effect

According to the disclosed measuring method and measuring system of bromate ion concentration, the bromate ion concentration in a water sample can be measured at a high accuracy.

BRIEF DESCRIPTION OF THE DRAWINGS

In the accompanying drawing:
The FIGURE is a diagram illustrating a schematic configuration of a representative measuring system of bromate ion concentration according to this disclosure.

DETAILED DESCRIPTION

Figure 1:
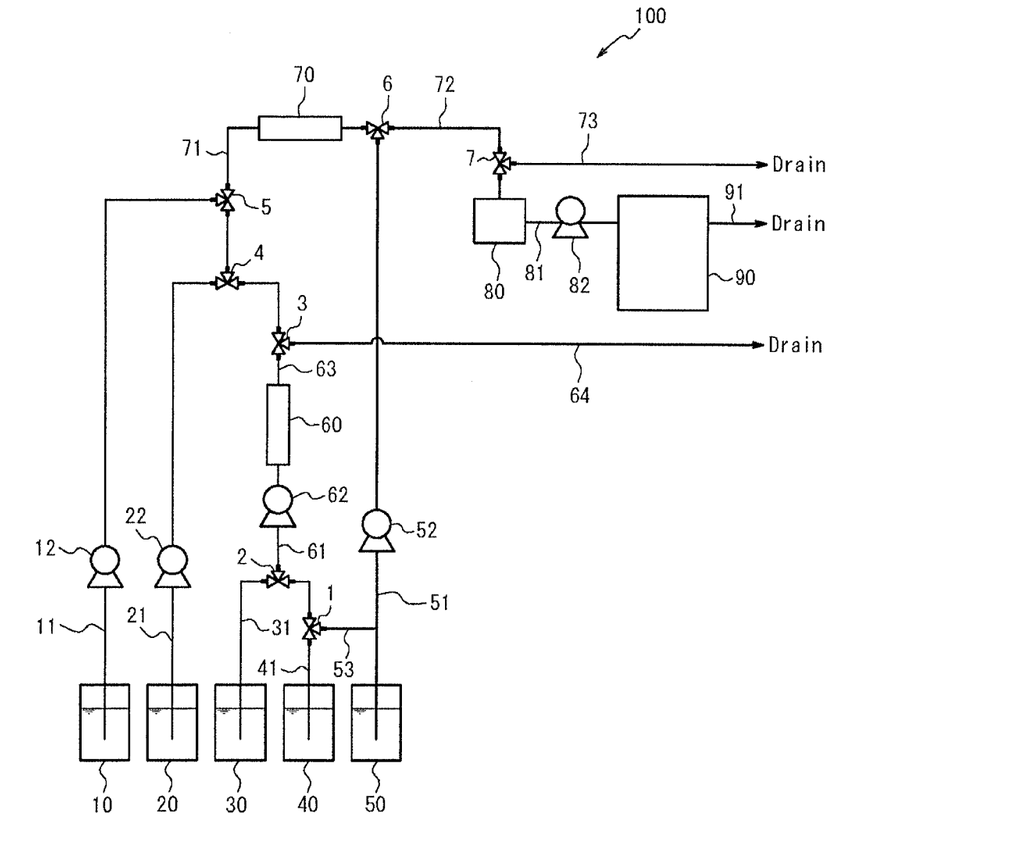

The following describes an embodiment of this disclosure with reference to the drawing.

Here, the measuring method and the measuring system of bromate ion concentration of this disclosure are not limited in particular, and can be used to measure the concentration of bromate ions contained in a water sample such as purified water produced by employing an advanced water treatment such as an ozone-activated carbon treatment, for example.

(Measuring Method of Bromate Ion Concentration)

The disclosed measuring method of bromate ion concentration is a quantitative method (fluorescence method) using a fluorescent substance such as trifluoperazine (TFP) and the like whose fluorescence intensity changes in response to the bromate ion concentration. Furthermore, in order to prevent the measured value of fluorescence intensity from being influenced by an interfering substance such as iodate ions and the like, the disclosed measuring method of bromate ion concentration uses a technique of measuring the fluorescence intensity and calculating the bromate ion concentration in the water sample after separating and concentrating bromate ions by using an anion exchanger that selectively adsorbs bromate ions. Further, in one example of the disclosed measuring method of bromate ion concentration, the following processes (1) to (4) are repeatedly performed to continuously measure the bromate ion concentration contained in the water samples.

(1) A first fluorescence intensity measuring process including a process of passing a water sample through an anion exchanger that adsorbs bromate ions, a process of passing hydrochloric acid through the anion exchanger to elute the bromate ions adsorbed to the anion exchanger into the hydrochloric acid, and a process of measuring the fluorescence intensity of the hydrochloric acid passed through the anion exchanger;

(2) A second fluorescence intensity measuring process including a process of passing a water sample through an anion exchanger that adsorbs bromate ions, a process of passing a hydrochloric acid solution containing a fluorescent substance whose fluorescence intensity changes due to the coexistence of bromate ions through the anion exchanger to elute bromate ions adsorbed to the anion exchanger into the hydrochloric acid solution, and a process of measuring the fluorescence intensity of the hydrochloric acid solution passed through the anion exchanger;

(3) A calculation process of calculating the difference between the fluorescence intensity of the hydrochloric acid solution measured in the second fluorescence intensity measuring process and that of the hydrochloric acid measured in the first fluorescence intensity measuring process; and (4) A bromate ion concentration determination process of determining the bromate ion concentration in the water sample by using the difference between the fluorescence intensities calculated in the calculation process and a calibration curve.

It should be noted that, in one example of the disclosed measuring method of bromate ion concentration, when measuring the bromate ion concentration contained in the water sample, it does not matter which of the first fluorescence intensity measuring process and the second fluorescence intensity measuring process is performed first.

Furthermore, an anion exchanger that does not adsorb iodate ions and the like but selectively adsorbs bromate ions is not limited to a specific one, and a strong anion-exchange column and the like having a polymer to which a hydrophobic property reduction treatment has been applied as a base material and quaternary amine as a functional group may be used.

<First Fluorescence Intensity Measuring Process>

In the first fluorescence intensity measuring process, the fluorescence intensity of the solution obtained by separating and concentrating bromate ions in the water sample is measured in the same manner as the second fluorescence intensity measuring process explained in detail below, except for the measurement of fluorescence intensity in the absence of a fluorescent substance (TFP and the like).

More specifically, in the first fluorescence intensity measuring process, first, a water sample is passed through an anion exchanger that adsorbs bromate ions to selectively adsorb bromate ions contained in the water sample to the anion exchanger. It should be noted that when a water sample contains a substance (a substance having a higher binding capacity to an anion exchanger than bromate ions) such as chloride ions that prevent bromate ions from being adsorbed to the anion exchanger, it is preferable to remove the interfering substances from the water sample by using a column for removing salt (e.g. Ag/H column, which is a combination of a silver form cation exchange column and a hydrogen form cation exchange column) and the like before it is passed through the anion exchanger.

Next, in the first fluorescence intensity measuring process, the hydrochloric acid containing no fluorescent substance is passed through the anion exchanger to elute bromate ions adsorbed to the anion exchanger into the hydrochloric acid. It should be noted that, hydrochloric acid with a concentration that allows bromate ions adsorbed to the anion exchanger to be eluted sufficiently can be used. More specifically, hydrochloric acid with a concentration of 1 to 6 mol/L can be used.

Then finally, in the first fluorescence intensity measuring process, the fluorescence intensity of the hydrochloric acid (the hydrochloric acid containing eluted bromate ions) passed through the anion exchanger is measured in the absence of fluorescent substance.

It should be noted that the measurement of the fluorescence intensity is not limited in particular, and measurement can be made by using, for example, a spectrofluorophotometer RF-5300PC made by the Shimazu Corporation, and the like. Further, a combination of excitation wavelength and emission wavelength for measuring the fluorescence intensity can be appropriately set according to the fluorescent substance used in the second fluorescence intensity measuring process. More specifically, when TFP is used as a fluorescent substance in the second fluorescence intensity measuring process, as a combination of excitation wavelength and emission wavelength, "excitation wavelength: 264 nm, emission wavelength: 400 nm," "excitation wavelength: 300 nm, emission wavelength: 400 nm," "excitation wavelength: 264 nm, emission wavelength: 480 nm" or "excitation wavelength: 300 nm, emission wavelength: 480 nm" may be adopted.

<Second Fluorescence Intensity Measuring Process>

Further, in the second fluorescence intensity measuring process, the bromate ion concentration in a water sample is measured in the same manner as that in the first fluorescence intensity measuring process, except for the measurement of fluorescence intensity in the presence of fluorescent substance (TFP and the like). That is, in the second fluorescence intensity measuring process, the fluorescence intensity of the solution obtained by separating and concentrating bromate ions in a water sample is measured in the same manner as that in the first fluorescence intensity measuring process except for the use of a hydrochloric acid solution containing a fluorescent substance such as TFP and the like where hydrochloric acid containing no fluorescent substance is used instead.

More specifically, in the second fluorescence intensity measuring process, first, a water sample is passed through an anion exchanger that adsorbs bromate ions to selectively adsorb the bromate ions contained in the water sample to the anion exchanger. It should be noted that, when a substance that prevents bromate ions from being adsorbed to the anion exchanger is contained in a water sample, it is preferable to remove the interfering substances from the water sample before it is passed through the anion exchanger, a same manner as that in the first fluorescence intensity measuring process.

Here, in the second fluorescence intensity measuring process, it is preferable that the same water sample as used in the first fluorescence intensity measuring process is used by, for example storing the required amount of water sample both for the first fluorescence intensity measuring process and the second fluorescence intensity measuring process beforehand. However, in the case where the first fluorescence intensity measuring process and the second fluorescence intensity measuring process are continuously performed, it is not necessary to use identical water samples in the first fluorescence intensity measuring process and the second fluorescence intensity measuring process if the water quality of the samples does not change considerably over a short period of time, such as the water sample from a water purification plant for continuous measurement of the bromate ion concentration. That is, water samples sampled at different timings may be used in the first fluorescence intensity measuring process and the second fluorescence intensity measuring process by sequentially performing the first fluorescence intensity measuring process and the second fluorescence intensity measuring process while continuously sampling water samples.

Next, in the second fluorescence intensity measuring process, a hydrochloric acid solution obtained by mixing a fluorescent substance such as TFP and the like and hydrochloric acid is passed through the anion exchanger to elute bromate ions adsorbed to the anion exchanger into the hydrochloric acid solution. It should be noted that the concentration of hydrogen chloride in the hydrochloric acid solution is the same as that of the hydrochloric acid used in the first fluorescence intensity measuring process. Further, the concentration of the fluorescent substance in the hydrochloric acid solution is not limited in particular, and the concentration may be those used generally in the measurement of the bromate ion concentration using the fluorescence method.

Then, finally, in the second fluorescence intensity measuring process, the fluorescence intensity of the hydrochloric acid solution passed through the anion exchanger (the hydrochloric acid solution that contains eluted bromate ions and the fluorescent substance) is measured in the same manner as that in the first fluorescence intensity measuring process.

It should be noted that, under the condition where TFP is present as a fluorescent substance, a fluorescence reaction occurs in which the fluorescence intensity increases as the bromate ion concentration increases when the emission wavelength is 400 nm, and a quenching reaction occurs in which the fluorescence intensity decreases as the bromate ion concentration increases when the emission wavelength is 480 nm.

<Calculation Process>

In the calculation process, the difference between the fluorescence intensity of the hydrochloric acid solution measured in the second fluorescence intensity measuring process and the fluorescence intensity of the hydrochloric acid measured in the first fluorescence intensity measuring process is calculated. That is, in the calculation process, the difference between the fluorescence intensity measured under the condition where the separated and concentrated bromate ions and the fluorescent substance cause a fluorescence reaction or a quenching reaction and that measured under the condition where a fluorescence reaction or a quenching reaction based on the separated and concentrated bromate ions does not occur is calculated.

<Bromate Ion Concentration Determination Process>

In the bromate ion concentration determination process, the bromate ion concentration in the water sample is calculated by using the difference between the fluorescence intensities calculated in the calculation process, and a calibration curve as well. More specifically, in the bromate ion concentration determination process, first, the bromate ion concentration in the water sample is determined by using a calibration curve indicating a relationship between the fluorescence intensities and the bromate ion concentrations prepared by using the standard water samples that contain bromate ions with known concentrations. It should be noted that, when the amount of water sample passed through the anion exchanger in the first fluorescence intensity measuring process and the second fluorescence intensity measuring process differs from that of standard water samples passed through the anion exchanger for preparing the calibration curve, the bromate ion concentration in the water sample should be determined in consideration of the concentration rate.

Further, according to the above described example of the disclosed measuring method of the bromate ion concentration, the bromate ion concentration in a water sample is determined by using the difference between the fluorescence intensity of the hydrochloric acid solution measured in the second fluorescence intensity measuring process and that of the hydrochloric acid measured in the first fluorescence intensity measuring process. Thus, compared with the case where the bromate ion concentration is determined by using only the fluorescence intensity of the hydrochloric acid solution or with the case where the bromate ion concentration is determined by subtracting what is called a blank value from the fluorescence intensity of the hydrochloric acid solution, the measuring accuracy of bromate ion concentration can be improved. It should be noted that, in this specification, the "blank value" refers to the fluorescence intensity measured by irradiating excitation light to a water sample or ultrapure water, or one measured by irradiating excitation light to a blank measurement cell.

Here, the reason why the measuring accuracy can be improved by using the difference between the fluorescence intensity of the hydrochloric acid solution measured in the second fluorescence intensity measuring process and that of the hydrochloric acid measured in the first fluorescence intensity measuring process is assumed as follows.

That is, traditionally, it is believed that, when separation and concentration of bromate ions are performed by using an anion exchanger that selectively adsorbs bromate ions, the fluorescence intensity can be measured without being influenced by interfering substances such as iodate ion and the like. However, the inventors of this disclosure have examined the measuring performance and found out that, besides bromate ions, a coexisting substance which is excited and emits light when it is exposed to the excitation light can also be adsorbed to the anion exchanger. And the inventors have also found out that the coexisting substance adsorbed to the anion exchanger can be desorbed together with bromate ions when the hydrochloric acid solution is passed through it. Therefore, when the bromate ion concentration is determined by using only the fluorescence intensity of the hydrochloric acid solution or when the bromate ion concentration is determined by subtracting what is called a blank value from the fluorescence intensity of the hydrochloric acid solution, the influence of the light emitted by the coexisting substance itself (in other words, the coexisting substance itself concentrated by the anion exchanger) contained in the hydrochloric acid solution on the fluorescence intensity, and the decline in the measuring accuracy cannot be prevented. However, in one example of the disclosed measuring method of bromate ion concentration, the magnitude of fluorescence intensity due to the light emission of the coexisting substances desorbed from the anion exchanger is measured in the first fluorescence intensity measuring process, and the bromate ion concentration is determined by using the difference between the fluorescence intensity of the hydrochloric acid solution measured in the second fluorescence intensity measuring process and that of the hydrochloric acid measured in the first fluorescence intensity measuring process. Therefore, the influence of the coexisting substances is reduced or removed, and the bromate ion concentration can be measured with similar accuracy to that the official method (IC-PC method) achieves. Further, in one example of the disclosed measuring method of bromate ion concentration, the bromate ion concentration can be measured with high accuracy with respect to water samples having water qualities (in particular, the concentration of coexisting substances) different from each other, and as a result of this, even water samples are collected from different places, for example, the bromate ion concentrations of the water samples can still be measured with high accuracy regardless of their sampling places, thus the disclosed measuring method of bromate ion concertation is highly applicable to water samples having various water qualities.

It should be noted that, the reason why the influence of coexisting substances can be reduced or removed merely by calculating the difference between the fluorescence intensity of the hydrochloric acid solution measured in the second fluorescence intensity measuring process and that of the hydrochloric acid measured in the first fluorescence intensity measuring process without performing complicated work to determine the amount of coexisting substances is assumed that, unlike bromate ions, the coexisting substances do not have an influence on the fluorescent substance such as TFP, thus they do not change the fluorescence intensity. While on the other hand, the existence of TFP does not have a significant influence on the amount of bromate ions eluted from the anion exchanger.

Further, according to the above described one example of the disclosed measuring method of bromate ion concentration, the first fluorescence intensity measuring process, the second fluorescence intensity measuring process, the calculation process and the bromate ion concentration determination process are continuously and repeatedly performed. Therefore, even if each water sample sampled at timings different from each other is used in the first fluorescence intensity measuring process and the second fluorescence intensity measuring process, influence of each water sample due to change of its water quality over the time is reduced, and the bromate ion concentration in the water sample can be measured with high accuracy.

It should be noted that, as a calibration curve used by the disclosed measuring method of bromate ion concentration, any calibration curve indicating a relationship between fluorescence intensities and bromate ion concentrations can be used. However, from the aspect of measurement of the bromate ion concentration in a water sample with higher accuracy, it is preferable that a calibration curve obtained by performing the calibration curve preparation process explained below is used.

<Calibration Curve Preparation Process>

In the calibration curve preparation process, a third fluorescence intensity measuring process and a fourth fluorescence intensity measuring process described below are performed respectively, to a plurality of standard water samples with bromate ion concentrations different from each other. Further, a calibration curve indicating a relationship between bromate ion concentrations and the differences between the fluorescence intensities is prepared by using the fluorescence intensity of the hydrochloric acid solution measured in the fourth fluorescence intensity measuring process and that of the hydrochloric acid measured in the third fluorescence intensity measuring process.

[Third Fluorescence Intensity Measuring Process]

In the third fluorescence intensity measuring process, the fluorescence intensity of the hydrochloric acid is measured in the same manner as that in the first fluorescence intensity measuring process except for the use of a standard water sample with a known concentration instead of a water sample. More specifically, in the third fluorescence intensity measuring process, first, a standard water sample with a known concentration is passed through an anion exchanger that adsorbs bromate ions, and the bromate ions in the standard water sample are adsorbed to the anion exchanger. Next, hydrochloric acid is passed through the anion exchanger to elute the bromate ions adsorbed to the anion exchanger into the hydrochloric acid. And finally, the fluorescence intensity of the hydrochloric acid passed through the anion exchanger viz. the hydrochloric acid containing eluted bromate ions but without fluorescent substance is measured. It should be noted that, it is allowed for the standard water sample to be passed through a column to remove the salts in it before it is subjected to be passed through the anion exchanger, a similar operation applied to the water samples in the first fluorescence intensity measuring process.

[Fourth Fluorescence Intensity Measuring Process]

In the fourth fluorescence intensity measuring process, the fluorescence intensity of the hydrochloric acid is measured in the same manner as that in the second fluorescence intensity measuring process except for the use of a standard water sample with a known concentration instead of a water sample. More specifically, in the fourth fluorescence intensity measuring process, first, a standard water sample with a known concentration is passed through an anion exchanger that adsorbs bromate ions, and the bromate ions in the standard water sample are adsorbed to the anion exchanger. Next, a hydrochloric acid solution obtained by mixing a fluorescent substance such as TFP and the like and hydrochloric acid is passed through the anion exchanger to elute bromate ions adsorbed to the anion exchanger into the hydrochloric acid solution. And finally, the fluorescence intensity of the hydrochloric acid solution (the hydrochloric acid solution containing the eluted bromate ions and the fluorescent substance) passed through the anion exchanger is measured. It should be noted that, it is allowed for the standard water sample to be passed through a column for removing salt before it is passed through the anion exchanger, a similar operation applied to the water sample in the second fluorescence intensity measuring process.

(Measuring System of Bromate Ion Concentration)

It should be noted that the measurement of bromate ion concentration using the disclosed measuring method of bromate ion concentration described above can be performed by using the disclosed measuring system of bromate ion concentration.

Here, the FIGURE illustrates one example of the disclosed measuring system of bromate ion concentration. The measuring system 100 illustrated in the FIGURE includes a first vessel 10 that stores a hydrochloric acid solution containing a fluorescent substance such as TFP and the like, a second vessel 20 that stores hydrochloric acid, a third vessel 30 that stores a water sample, a fourth vessel 40 that stores a standard water sample with an arbitrary bromate ion concentration and a fifth vessel 50 that stores ultrapure water. Further, the measuring system 100 includes a Ag/H column 60 as a column for removing salt, an anion-exchange column 70 as an anion exchanger that adsorbs bromate ions, a centrifuge tube 80 that temporarily stores a certain amount of liquid passed through the anion-exchange column 70 and a fluorescence intensity measuring device 90 that measures the fluorescence intensity of the liquid passed through the centrifuge tube 80. Further, the measuring system 100 includes a bromate ion concentration determination device (not illustrated) having a calculation unit that operates calculations by using the fluorescence intensity measured by the fluorescence intensity measuring device 90, and a storage unit that stores a calibration curve. It should be noted that, in the FIGURE, although only one vessel is illustrated as the fourth vessel 40, the fourth vessel 40 may be configured with a plurality of vessels that store standard water samples with concentrations different from each other.

The measuring system 100 also includes a hydrochloric acid solution line 11 that has a hydrochloric acid solution pump 12 and connects the first vessel 10 and a three-way valve 5, a hydrochloric acid line 21 that has a hydrochloric acid pump 22 and connects the second vessel 20 and a three-way valve 4, a water sample line 31 that connects the third vessel 30 and the three-way valve 2, a standard water sample line 41 that has a three-way valve 1 and connects the fourth vessel 40 and the three-way valve 2, and a washing line 51 that has a washing pump 52 and connects the fifth vessel 50 and a three-way valve 6. It should be noted that an ultrapure water line 53 is branched off from the washing line 51 located between the fifth vessel 50 and the washing pump 52. Further, the ultrapure water line 53 connects the three-way valve 1 provided at the standard water sample line 41 and the washing line 51.

The measuring system 100 also includes a salt removing line 61 that has a salt removing pump 62 connecting the three-way valve 2 and the Ag/H column 60, a desalination line 63 that has a three-way valve 3 connecting the Ag/H column 60 and the three-way valve 4, an anion-exchange line 71 that has the three-way valve 5 connecting the anion-exchange column 70 and the three-way valve 4, an effluent line 72 that has the three-way valve 6 and the three-way valve 7 connecting the anion-exchange column 70 and the centrifuge tube 80, a measuring line 81 that has a measuring pump 82 connecting the centrifuge tube 80, and the fluorescence intensity measuring device 90.

The measuring system 100 further includes a drain line 64 with its one end thereof connecting to the three-way valve 3, a drain line 73 with its one end thereof connecting to the three-way valve 7 and a drain line 91 that transfers drain discharged from the fluorescence intensity measuring device 90.

Thus, in the measuring system 100 having the above described configuration can measure the bromate ion concentration in a water sample as described below, for example.

<Preparation of a Calibration Curve>

More specifically, in the measuring system 100, the flow passages are controlled by using the three-way valves 1 to 7, and the standard water sample in the fourth vessel 40 is passed through the Ag/H column 60 and the anion-exchange column 70 in a sequential order so that bromate ions in the standard water sample is adsorbed to the anion-exchange column 70. It should be noted that the liquid passed through the anion-exchange column 70 is discharged out of the system from the drain line 73.

Here, when the above described operation is performed, the three-way valves 1 to 7, the fourth vessel 40, the standard water sample line 41, the Ag/H column 60, the salt removing line 61, the salt removing pump 62, the desalination line 63, the anion-exchange line 71, the effluent line 72 and the drain line 73 serve as a standard water sample supply device to pass the standard water sample with a known concentration through the anion-exchange column 70 serving as an anion exchanger.

Next, the flow passages are controlled by using the three-way valves 1 to 7 to pass the hydrochloric acid in the second vessel 20 through the anion-exchange column 70 to elute the bromate ions adsorbed to the anion-exchange column 70 into the hydrochloric acid. Then the hydrochloric acid containing bromate ions is temporarily stored in the centrifuge tube 80.

Here, when the above described operation is performed, the three-way valves 1 to 7, the second vessel 20, the hydrochloric acid line 21, the hydrochloric acid pump 22, the anion-exchange line 71, the effluent line 72 and the centrifuge tube 80 serve as a hydrochloric acid supply device to pass the hydrochloric acid through the anion-exchange column 70 serving as an anion exchanger.

After that, the hydrochloric acid stored in the centrifuge tube 80 is supplied to the fluorescence intensity measuring device 90 via the measuring line 81 and the measuring pump 82, and the fluorescence intensity of the hydrochloric acid is measured.

Further, after the flow passages concerned in the measuring system 100 being washed by arbitrarily using ultrapure water in the fifth vessel, the bromate ions in the standard water sample is adsorbed to the anion-exchange column 70 in the same manner as described above.

Next, the flow passages are controlled by using the three-way valves 1 to 7 and the hydrochloric acid solution in the first vessel 10 is passed through the anion-exchange column 70 to elute bromate ions adsorbed to the anion-exchange column 70 into the hydrochloric acid solution. Then the hydrochloric acid solution containing the bromate ions is temporarily stored in the centrifuge tube 80.

Here, when the above described operation is performed, the three-way valves 1 to 7, the first vessel 10, the hydrochloric acid solution line 11, the hydrochloric acid solution pump 12, the anion-exchange line 71, the effluent line 72 and the centrifuge tube 80 serve as a hydrochloric acid solution supply device to pass the hydrochloric acid solution through the anion-exchange column 70.

After that, the hydrochloric acid solution stored in the centrifuge tube 80 is supplied to the fluorescence intensity measuring device 90 via the measuring line 81 and the measuring pump 82, and the fluorescence intensity of the hydrochloric acid solution is measured.

Then, in the measuring system 100, the above described operation is repeatedly performed for the standard water samples with concentrations different from each other. Further, in the measuring system 100, for standard water samples with concentrations different from each other, the difference between the fluorescence intensity of the hydrochloric acid solution and the fluorescence intensity of the hydrochloric acid is calculated by the calculation unit to prepare a calibration curve indicating a relationship between the bromate ion concentration and the difference between the fluorescence intensities, and the calibration curve is stored in the storage unit.

<Measurement of Bromate Ion Concentration>

Further, after the flow passages concerned in the measuring system 100 being washed by arbitrarily using the ultrapure water in the fifth vessel, by using the three-way valves 1 to 7 to control the flow passages, the water sample in the third vessel 30 is sequentially passed through the Ag/H column 60 and the anion-exchange column 70 to have the bromate ions in the water sample adsorbed to the anion-exchange column 70. It should be noted that the liquid passed through the anion-exchange column 70 is discharged out of the system from the drain line 73.

Here, in the above described operation, the three-way valves 1 to 7, the third vessel 30, the water sample line 31, the Ag/H column 60, the salt removing line 61, the salt removing pump 62, the desalination line 63, the anion-exchange line 71, the effluent line 72 and the drain line 73 are used to serve as a water sample supply device to pass water sample through the anion-exchange column 70 serving as an anion exchanger.

Next, the flow channel is controlled by using the three-way valves 1 to 7 to control the flow passages, hydrochloric acid in the second vessel 20 is passed through the anion-exchange column 70 to elute the bromate ions adsorbed to the anion-exchange column 70 into the hydrochloric acid. Then the hydrochloric acid containing bromate ions is stored temporarily in the centrifuge tube 80.

After that, the hydrochloric acid stored in the centrifuge tube 80 is supplied to the fluorescence intensity measuring device 90 via the measuring line 81 and the measuring pump 82, and the fluorescence intensity of the hydrochloric acid is measured.

Further, after the flow passages concerned in the measuring system 100 being washed by arbitrarily using the ultrapure water in the fifth vessel, the bromate ions in the water sample are adsorbed to the anion-exchange column 70 in the same manner as described above.

Next, by using the three-way valves 1 to 7 to control the flow passages, the hydrochloric acid solution in the first vessel 10 is passed through the anion-exchange column 70 to elute the bromate ions adsorbed to the anion-exchange column 70 into the hydrochloric acid solution. Then the hydrochloric acid solution containing bromate ions is temporarily stored in the centrifuge tube 80.

After that, hydrochloric acid solution stored in the centrifuge tube 80 is supplied to the fluorescence intensity measuring device 90 via the measuring line 81 and the measuring pump 82, and the fluorescence intensity of the hydrochloric acid solution is measured.

Then, the calculation unit in the bromate ion concentration determination device (not illustrated) of the measuring system 100 calculates the difference between the fluorescence intensity of the hydrochloric acid solution and that of the hydrochloric acid measured by the fluorescence intensity measuring device 90 and the bromate ion concentration of the water sample is determined by using the difference between the fluorescence intensities calculated by the calculation unit and the calibration curve stored in the storage unit.

As described above, although the disclosed measuring method and measuring system are explained by using one example, the disclosed measuring method and measuring system are not limited to the above described example, and modifications may be arbitrarily added to the disclosed measuring method and measuring system.

In particular, in the above described measuring system 100, although the first vessel 10 is provided as a storage tank for storing a hydrochloric acid solution prepared by mixing a fluorescent substance and hydrochloric acid, a high accuracy metering pump may be incorporated into the system to prepare the hydrochloric acid solution by mixing a fluorescent substance and hydrochloric acid. However, from the aspect of facility cost as well as ease and stability of operation for adjusting the concentration of the fluorescent substance in the hydrochloric acid solution, it is preferable that the first vessel 10 is provided.

Further, the calibration curve stored in the storage unit is not limited to those prepared by using the above described method.

Furthermore, in the measuring system 100, operation of each pump and each three-way valve may be automatically controlled by using a control device or manually controlled.

EXAMPLES

Example 1

Four samples of ozone-activated carbon treated clean water collected from a water purification plant were defined as water samples A to D, and by using the measuring system 100 illustrated in the FIGURE, their bromate ion concentrations were measured by the fluorescence method, and respective error rate (={(the value measured by the fluorescence method−the value measured by the official method)/the value measured by the official method}×100%) was calculated by comparing the value measured by the fluorescence method and the value measured by the official method (IC-PC method). The results are shown in Table 1.

The measurement of the bromate ion concentration using the fluorescence method in this example was performed under the measuring conditions and by following the measuring procedures described below.

<Measuring Conditions>
Fluorescent substance: TFP
Hydrochloric acid: Concentration of hydrogen chloride 1 mol/L
Hydrochloric acid solution: Concentration of hydrogen chloride 1 mol/L,
TFP concentration 30 μmol/L
Excitation light wavelength: 300 nm
Emission wavelength: 400 nm
Ag/H column: OnGuard II® Ag/H made by Thermo Fisher Scientific Inc.
Anion-exchange column: MetaSEP IC-MA made by GL Sciences Inc.

<Measuring Procedures>
1. With respect to a standard water sample, a calibration curve was prepared by measuring only the fluorescence intensity of a hydrochloric acid solution passed through the anion-exchange column to elute bromate ions.
2. With respect to a water sample, the fluorescence intensity of the hydrochloric acid passed through the anion-exchange column to elute bromate ions and the fluorescence intensity of the hydrochloric acid solution passed through the anion-exchange column to elute bromate ions were measured, and the bromate ion concentration was determined by using the difference between the measured fluorescence intensities and a calibration curve as well.

Example 2

The bromate ion concentrations of the same water samples described in Example 1 were measured using the fluorescence method in the same manner as described in Example 1 except for the measuring conditions and the measuring procedures described below, and the error rate of each sample was calculated by comparing the value with that measured by using the official method (IC-PC method). The results are shown in Table 1.

<Measuring Conditions>
Fluorescent substance: TFP
Hydrochloric acid: Concentration of hydrogen chloride 1 mol/L
Hydrochloric acid solution: Concentration of hydrogen chloride 1 mol/L, TFP concentration 30 μmol/L
Excitation light wavelength: 300 nm
Emission wavelength: 400 nm
Ag/H column: OnGuard II® Ag/H made by Thermo Fisher Scientific Inc.
Anion-exchange column: MetaSEP IC-MA made by GL Sciences Inc.

<Measuring Procedures>
1. With respect to a standard water sample, the fluorescence intensity of hydrochloric acid passed through the anion-exchange column to elute bromate ions and the fluorescence intensity of a hydrochloric acid solution passed through the anion-exchange column to elute bromate ions were measured, and a calibration curve was prepared by using the differences between the measured fluorescence intensities.
2. With respect to a water sample, the fluorescence intensity of the hydrochloric acid passed through the anion-exchange column to elute bromate ions and the fluorescence intensity of the a hydrochloric acid solution passed through the anion-exchange column to elute bromate ions were measured, and the bromate ion concentration was determined by using the difference between the measured fluorescence intensities and a calibration curve as well.

Comparative Example 1

Four samples of ozone-activated carbon treated clean water obtained from a water purification plant were defined as water samples A to D, and the bromate ion concentrations were measured by the fluorescence method in a measuring system having a similar configuration to measuring system 100 illustrated in the FIGURE, except for that this measuring system does not have the second vessel 20, the hydrochloric acid line 21, the hydrochloric acid pump 22 and the three-way valve 4, but is provided with a line that directly supplies a water sample to the fluorescence intensity measuring device 90. And the error rate was calculated by comparing the values measured by the fluorescence method with those measured by the official method (IC-PC method). The results are shown in Table 1.

Measurement of the bromate ion concentrations using the fluorescence method was performed under the measuring conditions and by following the measuring procedures described below.

<Measuring Conditions>
Fluorescent substance: TFP
Hydrochloric acid solution: Concentration of hydrogen chloride 1 mol/L,
TFP concentration 30 mol/L
Excitation light wavelength: 300 nm
Emission wavelength: 400 nm
Ag/H column: OnGuard II® Ag/H made by Thermo Fisher Scientific Inc.
Anion-exchange column: MetaSEP IC-MA made by GL Sciences Inc.

<Measuring Procedures>
1. With respect to a standard water sample, a calibration curve was prepared by using only the fluorescence intensities of hydrochloric acid solutions passed through the anion-exchange column to elute bromate ions.
2. With respect to a water sample, the fluorescence intensity of hydrochloric acid passed through the anion-exchange column to elute bromate ions and the fluorescence intensity (blank value) of a water sample supplied as it is to the fluorescence intensity measuring device 90 without passing through the Ag/H column and the anion-exchange column were measured, and the bromate ion concentration was calculated by using the difference between the measured fluorescence intensities and a calibration curve.

Comparative Example 2

Four samples of ozone-activated carbon treated clean water collected from a water purification plant were defined as water samples A to D, and their bromate ion concentrations were measured by the fluorescence method by using a measuring system having a similar configuration to measuring system 100 illustrated in the FIGURE, except for that this system does not have the second vessel 20, the hydrochloric acid line 21, the hydrochloric acid pump 22 and the three-way valve 4. And the error rate was calculated by comparing the value measured by the fluorescence method with those measured by the official method (IC-PC method). The results are shown in Table 1.

Measurement of the bromate ion concentrations using the fluorescence method was performed under the measuring conditions and by following the measuring procedures described below.

<Measuring Conditions>
Fluorescent substance: TFP
Hydrochloric acid solution: Concentration of hydrogen chloride 1 mol/L,
TFP concentration 30 μmol/L
Excitation light wavelength: 300 nm
Emission wavelength: 400 nm
Ag/H column: OnGuard II® Ag/H made by Thermo Fisher Scientific Inc.
Anion-exchange column: MetaSEP IC-MA made by GL Sciences Inc.

<Measuring Procedures>
1. With respect to a standard water sample, a calibration curve was prepared by using only the fluorescence intensities of hydrochloric acid solutions passed through the anion-exchange column to elute bromate ions.
2. With respect to a water sample, the bromate ion concentration was determined by using the fluorescence intensity of a hydrochloric acid solution passed through the anion-exchange column to elute bromate ions and a calibration curve as well.

change column to elute bromate ions from water samples was used, the bromate ion concentration is measured with even higher accuracy.

INDUSTRIAL APPLICABILITY

According to the disclosed measuring method and measuring system of the bromate ion concentration, the bromate ion concentration of water sample can be measured at a high accuracy.

REFERENCE SIGNS LIST

1 to 7 Three-way valve
10 First vessel
11 Hydrochloric acid solution line
12 Hydrochloric acid solution pump
20 Second vessel
21 Hydrochloric acid line
22 Hydrochloric acid pump
30 Third vessel
31 Water sample line
40 Fourth vessel
41 Standard water sample line
50 Fifth vessel
51 Washing line
52 Washing pump
53 Ultrapure water line
60 Ag/H column
61 Salt removing line
62 Salt removing pump
63 Desalination line
64 Drain line
70 Anion-exchange column
71 Anion-exchange line
72 Effluent line
73 Drain line
80 Centrifuge tube
81 Measuring line
82 Measuring pump
90 Fluorescence intensity measuring device
91 Drain line
100 Measuring system

TABLE 1

|  | Value measured by official method (μg/L) | Comparative Example 1 | | Comparative Example 2 | | Example 1 | | Example 2 | |
| --- | --- | --- | --- | --- | --- | --- | --- | --- | --- |
|  |  | Measured value (μg/L) | Error rate (%) | Measured value (μg/L) | Error rate (%) | Measured value (μg/L) | Error rate (%) | Measured value (μg/L) | Error rate (%) |
| Water sample A | 0.4 | −3.2 | −900.0 | 7.3 | 1725.0 | 0.0 | −100.0 | 0.5 | 25.0 |
| Water sample B | 0.6 | −1.6 | −366.7 | 3.1 | 416.7 | 1.5 | 150.0 | 0.8 | 33.3 |
| Water sample C | 2.4 | 1.2 | −50.0 | 7.3 | 204.2 | 2.4 | 0.0 | 2.7 | 12.5 |
| Water sample D | 9.0 | 5.9 | −34.4 | 13.1 | 45.6 | 8.6 | −4.4 | 8.8 | −2.2 |

Table 1 showed that, compared with those in Comparative Examples 1 and 2, the values of the bromate ion concentrations in Example 1 and 2, were closer to the values measured by the official method (that is, the error rate was smaller), indicating the bromate ion concentration is measured with higher accuracy.

Table 1 further showed that, in Example 2 where a calibration curve prepared by using the differences between the fluorescence intensities of the hydrochloric acid and hydrochloric acid solution passed through the anion-ex-

The invention claimed is:
1. A measuring method of bromate ion concentration, comprising:
a first fluorescence intensity measuring process including a process of passing a water sample from a water source through an anion exchanger that adsorbs bromate ions, a process of passing hydrochloric acid through the anion exchanger to elute bromate ions adsorbed to the anion exchanger into the hydrochloric acid, and a process of measuring a fluorescence intensity of the hydrochloric acid passed through the anion exchanger;

a second fluorescence intensity measuring process including a process of passing a water sample from the water source through an anion exchanger that adsorbs bromate ions, a process of passing a hydrochloric acid solution containing a trifluoperazine whose fluorescence intensity changes due to coexistence of bromate ions through the anion exchanger to elute bromate ions adsorbed to the anion exchanger into the hydrochloric acid solution, and a process of measuring a fluorescence intensity of the hydrochloric acid solution passed through the anion exchanger;

a calculation process of calculating a difference between the fluorescence intensity of the hydrochloric acid solution measured in the second fluorescence intensity measuring process and that of the hydrochloric acid measured in the first fluorescence intensity measuring process; and a bromate ion concentration determination process of determining a bromate ion concentration of the water sample by using a difference between the fluorescence intensities calculated in the calculation process and a calibration curve indicating a relationship between fluorescence intensities and known bromate ion concentrations.

2. The measuring method of bromate ion concentration according to claim 1, comprising:

a third fluorescence intensity measuring process including a process of passing a standard water sample of a same type with a known concentration through an anion exchanger that adsorbs bromate ions, a process of passing hydrochloric acid through the anion exchanger to elute bromate ions adsorbed to the anion exchanger into the hydrochloric acid, and a process of measuring a fluorescence intensity of the hydrochloric acid passed through the anion exchanger;

a fourth fluorescence intensity measuring process including a process of passing a standard water sample of the same type with a known concentration through an anion exchanger that adsorbs bromate ions, a process of passing a hydrochloric acid solution containing trifluoperazine whose fluorescence intensity changes due to coexistence of bromate ions through the anion exchanger to elute bromate ions adsorbed to the anion exchanger into the hydrochloric acid solution, and a process of measuring a fluorescence intensity of the hydrochloric acid solution passed through the anion exchanger; and a calibration curve preparation process of performing the third fluorescence intensity measuring process and the fourth fluorescence intensity measuring process with respect to a plurality of standard water samples with known bromate ion concentrations different from each other to prepare the calibration curve by using a difference between the fluorescence intensity of the hydrochloric acid solution measured in the fourth fluorescence intensity measuring process and that of the hydrochloric acid measured in the third fluorescence intensity measuring process for the known bromate ion concentrations of each of the plurality of standard water samples.

3. The measuring method of bromate ion concentration according to claim 2, wherein the first fluorescence intensity measuring process, the second fluorescence intensity measuring process, the calculation process and the bromate ion concentration determination process are repeatedly performed to continuously measure a bromate ion concentration of the water sample.

4. The measuring method of bromate ion concentration according to claim 1, wherein the first fluorescence intensity measuring process, the second fluorescence intensity measuring process, the calculation process and the bromate ion concentration determination process are repeatedly performed to continuously measure a bromate ion concentration of the water sample.

5. A measuring system of bromate ion concentration, comprising:

an anion exchanger that adsorbs bromate ions;

a water sample supply device that passes a water sample through the anion exchanger;

a hydrochloric acid supply device that passes hydrochloric acid through the anion exchanger;

a hydrochloric acid solution supply device that passes a hydrochloric acid solution containing trifluoperazine whose fluorescence intensity changes due to coexistence of bromate ions through the anion exchanger;

a fluorescence intensity measuring device that measures a fluorescence intensity of a liquid passed through the anion exchanger; and a bromate ion concentration determination device that includes a calculation unit that calculates a difference between a fluorescence intensity of the hydrochloric acid solution measured by the fluorescence intensity measuring device and a fluorescence intensity of the hydrochloric acid measured by the fluorescence intensity measuring device and a storage unit that stores a calibration curve indicating a relationship between fluorescence intensities and known bromate ion concentrations, and determines a bromate ion concentration in the water sample by using differences between the fluorescence intensities calculated by the calculation unit and ache calibration curve stored in the storage unit.

6. The measuring system of bromate ion concentration according to claim 5, wherein the hydrochloric acid solution supply device comprises a storage tank for storing a hydrochloric acid solution obtained by mixing the trifluoperazine and the hydrochloric acid and a hydrochloric acid solution supply line that supplies the hydrochloric acid solution from the storage tank to the anion exchanger.

7. The measuring system of bromate ion concentration according to claim 6, further comprising:

a standard water sample supply device that passes a standard water sample with a known bromate ion concentration through the anion exchanger, wherein the storage unit stores a calibration curve prepared by using a difference between a fluorescence intensity of hydrochloric acid measured by the fluorescence intensity measuring device by passing hydrochloric acid through the anion exchanger using the hydrochloric acid supply device after a standard water sample with the known bromate ion concentration is passed through the anion exchanger from the standard water sample supply device and that of a hydrochloric acid solution measured by the fluorescence intensity measuring device by passing a hydrochloric acid solution through the anion exchanger by using the hydrochloric acid solution supply device after a standard water sample with the known bromate ion concentration is passed through the anion exchanger from the standard water sample supply device.

8. The measuring system of bromate ion concentration according to claim 5, further comprising:

a standard water sample supply device that passes a standard water sample with a known bromate ion concentration through the anion exchanger, wherein the storage unit stores a calibration curve prepared by using a difference between a fluorescence intensity of hydrochloric acid measured by the fluorescence intensity measuring device by passing hydrochloric acid through the anion exchanger using the hydrochloric acid supply device after a standard water sample with the known bromate ion concentration is passed through the anion exchanger from the standard water sample supply device and a fluorescence intensity of a hydrochloric acid solution measured by the fluorescence intensity measuring device by passing a hydrochloric acid solution through the anion exchanger by using the hydrochloric acid solution supply device after a standard water sample with the known bromate ion concentration is passed through the anion exchanger from the standard water sample supply device.

\* \* \* \* \*